United States Patent
Stout et al.

(10) Patent No.: US 11,896,787 B2
(45) Date of Patent: Feb. 13, 2024

(54) ANTI-ROTATION CATHETER DEVICES, SYSTEMS, AND METHODS

(71) Applicant: Becton, Dickinson and Company, Franklin Lakes, NJ (US)

(72) Inventors: Marty Stout, South Jordan, UT (US); Mohankumar Natesan, Bukit Batok (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 182 days.

(21) Appl. No.: 16/998,904

(22) Filed: Aug. 20, 2020

(65) Prior Publication Data
US 2021/0093835 A1 Apr. 1, 2021

Related U.S. Application Data

(60) Provisional application No. 62/908,308, filed on Sep. 30, 2019.

(51) Int. Cl.
*A61M 25/06* (2006.01)
*A61M 25/00* (2006.01)
*A61M 5/32* (2006.01)

(52) U.S. Cl.
CPC .... *A61M 25/0618* (2013.01); *A61M 25/0097* (2013.01); *A61M 25/0606* (2013.01); *A61M 5/3293* (2013.01); *A61M 25/0693* (2013.01); *A61M 2205/276* (2013.01)

(58) Field of Classification Search
CPC .......... A61M 25/0618; A61M 25/0097; A61M 25/0606; A61M 25/0693; A61M 2205/276; A61M 25/0637; A61M 5/3293
See application file for complete search history.

(56) References Cited

U.S. PATENT DOCUMENTS

| | | | |
|---|---|---|---|
| 4,362,156 | A | 12/1982 | Feller, Jr. et al. |
| 6,117,108 | A | 9/2000 | Woehr et al. |
| 8,496,623 | B2 | 7/2013 | Burkholz |
| 9,399,120 | B2 | 7/2016 | Burkholz |

(Continued)

FOREIGN PATENT DOCUMENTS

| | | |
|---|---|---|
| AT | 494920 T | 1/2011 |
| AU | 3091202 A | 6/2002 |

(Continued)

*Primary Examiner* — Katherine H Schwiker
*Assistant Examiner* — Robert F Allen
(74) *Attorney, Agent, or Firm* — Kirton McConkie; Whitney Blair; Kevin Stinger (57) ABSTRACT

A catheter assembly may include a catheter hub and a catheter tube, which may extend distally from the catheter hub. The catheter assembly may include a push tab and one or more ribs extending outwardly from an upper portion of the catheter hub. The ribs may be shorter in height than the push tab and proximal to the push tab. A needle assembly may include a needle hub, an introducer needle extending distally from the needle hub and through the catheter tube, and a grip coupled to the needle hub. The grip may include a face disposed outwardly from the push tab and the ribs. A grip of a user may contact the push tab, the ribs, and the face to reduce rotation between the catheter hub and the needle hub in response to distal advancement of the catheter hub.

16 Claims, 10 Drawing Sheets

(56) References Cited

U.S. PATENT DOCUMENTS

| | | | |
|---|---|---|---|
| 2002/0072711 A1* | 6/2002 | Cindrich | A61M 25/0643 604/164.08 |
| 2003/0050611 A1 | 3/2003 | Cindrich | |
| 2004/0024370 A1* | 2/2004 | Wilkinson | A61M 25/0618 604/263 |
| 2007/0270758 A1* | 11/2007 | Hanner | A61M 25/0625 604/177 |
| 2010/0106092 A1* | 4/2010 | Tanabe | A61B 17/3403 604/164.08 |
| 2013/0096504 A1* | 4/2013 | Walker | A61M 25/0618 604/164.08 |
| 2014/0364809 A1 | 12/2014 | Isaacson et al. | |
| 2017/0120009 A1* | 5/2017 | Garrison | A61M 25/0631 |
| 2017/0296782 A1* | 10/2017 | Bornhoft | A61M 25/0606 |
| 2018/0318557 A1* | 11/2018 | Burkholz | A61M 25/0637 |
| 2020/0001050 A1* | 1/2020 | Garrison | A61M 25/0612 |
| 2020/0038634 A1 | 2/2020 | Garrison et al. | |
| 2020/0330726 A1 | 10/2020 | Bornhoft et al. | |

FOREIGN PATENT DOCUMENTS

| | | |
|---|---|---|
| AU | 2016344420 A1 | 5/2018 |
| AU | 2017249040 A1 | 11/2018 |
| AU | 2018261521 A1 | 4/2019 |
| AU | 2019268130 A1 | 12/2019 |
| BR | PI0712661 A2 | 9/2012 |
| BR | 112018071104 A2 | 1/2019 |
| BR | 112019022075 A2 | 5/2020 |
| CA | 3002701 A1 | 5/2017 |
| CA | 3018769 A1 | 10/2017 |
| CA | 3038151 A1 | 11/2018 |
| CN | 101448543 A | 6/2009 |
| CN | 106620942 A | 5/2017 |
| CN | 107296997 A | 10/2017 |
| CN | 207168789 U | 4/2018 |
| CN | 207627677 U | 7/2018 |
| CN | 108785829 A | 11/2018 |
| CN | 208785540 U | 4/2019 |
| EP | 2019703 A1 | 2/2009 |
| EP | 3368118 A2 | 9/2018 |
| EP | 3432968 A1 | 1/2019 |
| EP | 3618912 A2 | 3/2020 |
| ES | 2355397 T3 | 3/2011 |
| JP | 2009538188 A | 11/2009 |
| JP | 5073739 B2 | 11/2012 |
| JP | 2018535750 A | 12/2018 |
| JP | 2019511313 A | 4/2019 |
| JP | 2019536540 A | 12/2019 |
| JP | 6785963 B2 | 11/2020 |
| KR | 20180134968 A | 12/2018 |
| SG | 11201802993 A | 5/2018 |
| SG | 11201807908 A | 10/2018 |
| SG | 11201902690 Y | 11/2019 |
| WO | 200245781 A2 | 6/2002 |
| WO | 2007139741 A1 | 12/2007 |
| WO | 2017074685 A2 | 5/2017 |
| WO | 2017180308 A1 | 10/2017 |
| WO | 2018204636 A2 | 11/2018 |

* cited by examiner

FIG. 6C

ANTI-ROTATION CATHETER DEVICES, SYSTEMS, AND METHODS

RELATED APPLICATIONS

This application claims the benefit of U.S. Provisional Patent Application No. 62/908,308, filed Sep. 30, 2019, and entitled ANTI-ROTATION CATHETER DEVICES, SYSTEMS, AND METHODS which is incorporated herein in its entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over a needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient.

In order to verify proper placement of the introducer needle and/or the intravenous catheter in the vasculature, a user generally confirms that there is flashback of blood, which may be visible to the user. In some instances, the introducer needle may include a notch disposed towards a distal end of the introducer needle, and in response to the distal tip of the introducer needle being positioned within the vasculature, blood may flow proximally through a needle lumen, exit the needle lumen through the notch, and then travel proximally between an outer surface of the introducer needle and an inner surface of the intravenous catheter.

Accordingly, where the intravenous catheter is at least partially transparent, the user may visualize a small amount of blood "flashback" and thereby confirm placement of the intravenous catheter within the vasculature. Presence of a vasculature entrance indicator, such as flashback, may facilitate successful placement of intravenous catheters. Once placement of the introducer needle within the vasculature has been confirmed, the user may temporarily occlude flow in the vasculature and withdraw the introducer needle, leaving the intravenous catheter in place for future blood withdrawal and/or fluid infusion.

Some catheter hubs are unstable and are prone to free spinning on the introducer needle during insertion of the intravenous catheter into the patient. Oftentimes, a catheter hub includes a push tab to aid in advancing the catheter hub. As the catheter hub advances, in some cases, the catheter hub experiences rolling where the catheter hub spins along the axis of the introducer needle. This can cause a problem when the push tab rotates out of reach of a finger of the user being used to advance the catheter hub.

In some cases an edge is provided on the catheter hub so that the user can advance the catheter hub regardless of its angular position. There is a concern in that the edge becomes quite uncomfortable to a patient when the catheter hub has been taped down at an insertion site of the intravenous catheter, thus forcing the edge against the patient's soft tissue.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to anti-rotation catheter devices, systems, and methods. In some embodiments, a catheter system may include a catheter assembly, which may include a catheter hub. In some embodiments, the catheter hub may include a distal end, a proximal end, a lumen extending through the distal end and the proximal end.

In some embodiments, the catheter assembly may include a catheter tube, which may extend distally from the distal end of the catheter hub. In some embodiments, the catheter assembly may include a push tab and one or more ribs extending outwardly from an upper portion of the catheter hub. In some embodiments, the ribs may be shorter in height than the push tab and proximal to the push tab. In some embodiments, the catheter hub may include a stepped or tapered outer surface disposed between the distal end of the catheter hub and the proximal end of the catheter hub.

In some embodiments, the catheter system may include a needle assembly, which may include a needle hub and an introducer needle extending distally from the needle hub and through the catheter tube. In some embodiments, the needle hub may include a first grip and/or a second grip. In some embodiments, the first grip may include a first face and/or the second grip may include a second face opposite the first face. In some embodiments, the first face and/or the second face may be positioned outwardly from the catheter hub and a body of the needle hub. In further detail, in some embodiments, the first face and/or the second face may be positioned further away from the longitudinal axis of the catheter system than an outer surface of the catheter hub and an outer surface of the body of the needle hub. In some embodiments, the body of the needle hub may be generally cylindrical.

In some embodiments, the push tab may be distal and/or proximate to the stepped or tapered outer surface. In some embodiments, the push tab distal and/or proximate the stepped or tapered outer surface may facilitate simultaneous placement of a first digit of a user on the push tab and a second digit and a third digit on the first face and the second face, respectively. In some embodiments, the push tab distal and/or proximate the stepped or tapered outer surface may facilitate accommodation of a length, position, and curvature of the first digit when the second digit and the third digit are placed on the first face and the second face, respectively. In some embodiments, the first digit of the user may push in a distal direction on the push tab to advance the catheter hub distally with respect to the needle hub, while the second digit and the third digit may remain generally stationary. In some embodiments, the first digit may be disposed between the second digit and the third digit on a hand of the user. The first digit may correspond to, for example, a pointer finger of the user.

In some embodiments, a diameter of the first face and/or a diameter of the second face may increase in a proximal direction. In some embodiments, the first face and/or the second face may be concave. Thus, in some embodiments, the first face and/or the second face may conform to a curvature of digits of the user. In some embodiments, the first face and/or the second face may include one or more protrusions, which may enhance a tactile feel for the user with regard to placement of the digits of the user and assist in maintaining the digits of the user on the first face and/or the second face.

In some embodiments, a distal-most rib of the plurality of ribs may be proximal and/or proximate the stepped or tapered outer surface. In these and other embodiments, the push tab and the ribs may conform to a curvature of the first digit, facilitating contact of the push tab and the ribs with the first digit. In some embodiments, the catheter assembly may include one or more wings, which may extend outwardly from the catheter hub. In some embodiments, the push tab and at least one of the ribs may be aligned with the wings, which may decrease a likelihood interference of the second digit and/or the third digit with any securement tape or dressing coupled to the wings.

In some embodiments, the needle hub may include a first elliptical face and/or the second elliptical face. In some embodiments, the first elliptical face and/or the second elliptical face may be positioned outwardly from the catheter hub and a body of the needle hub. In some embodiments, the first elliptical face may be angled with respect to the longitudinal axis of the catheter system such that a proximal end of the first elliptical face is positioned upwardly with respect to a distal end of the first elliptical face. In some embodiments, the second elliptical face may be angled with respect to the longitudinal axis of the catheter system such that a proximal end of the second elliptical face is positioned upwardly with respect to a distal end of the second elliptical face.

In some embodiments, the push tab may be proximal and/or proximate the stepped or tapered outer surface. In some embodiments, the push tab distal and/or proximate the stepped or tapered outer surface may facilitate simultaneous placement of a first digit of a user on the push tab and second and third digits on the first elliptical face and the second elliptical face, respectively. In some embodiments, the push tab distal and/or proximate the stepped or tapered outer surface may facilitate accommodation of a length, position, and curvature of the first digit when the second digit and the third digit are placed on the first elliptical face and the second elliptical face, respectively. In some embodiments, the first digit of the user may push in a distal direction on the push tab to advance the catheter hub distally with respect to the needle hub, and the second digit and the third digit may remain generally stationary.

In some embodiments, the first elliptical face and/or the second elliptical face may include one or more protrusions, which may enhance a tactile feel for the user with regard to placement of the digits of the user and assist in maintaining the digits of the user on the first elliptical face and/or the second elliptical face.

In some embodiments, the first elliptical face and the second elliptical face may be spaced apart by a grip body. In some embodiments, the first elliptical face and/or the second elliptical face may extend proximally beyond the grip body to form a notch, which may decrease a likelihood of the hand of the user contacting and/or applying pressure of a top of the needle hub.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Referring now to FIGS. 1A-3B, in some embodiments, a catheter system 10 may include a catheter assembly 12, which may include a catheter hub 14. In some embodiments, the catheter hub 14 may include a distal end 16, a proximal end 18, a lumen 20 extending through the distal end 16 and the proximal end 18.

In some embodiments, the catheter assembly 12 may include a catheter tube 22, which may extend distally from the distal end 16 of the catheter hub 14. In some embodiments, the catheter tube 22 may include a PIVC, a PICC, or a midline catheter tube. In some embodiments, the catheter assembly 12 may include a push tab 24 and one or more ribs 26 extending outwardly from an upper portion of the catheter hub 14. In some embodiments, the ribs 26 may be shorter in height than the push tab 24 and proximal to the push tab 24.

Figure 2A:
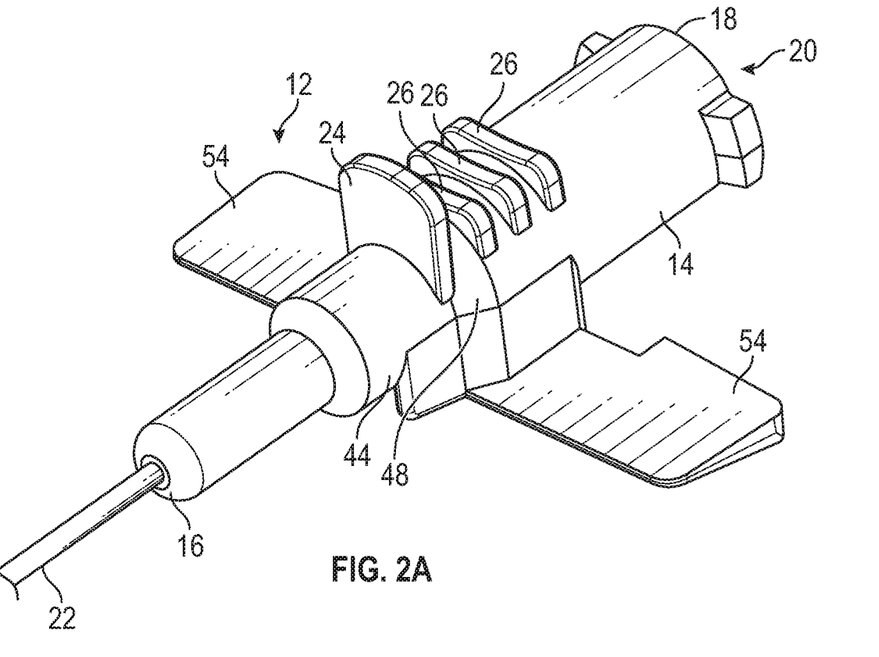
FIG. 2A is an upper perspective view of an example catheter hub of the catheter system of FIG. 1A, according to some embodiments.
Figure 2B:
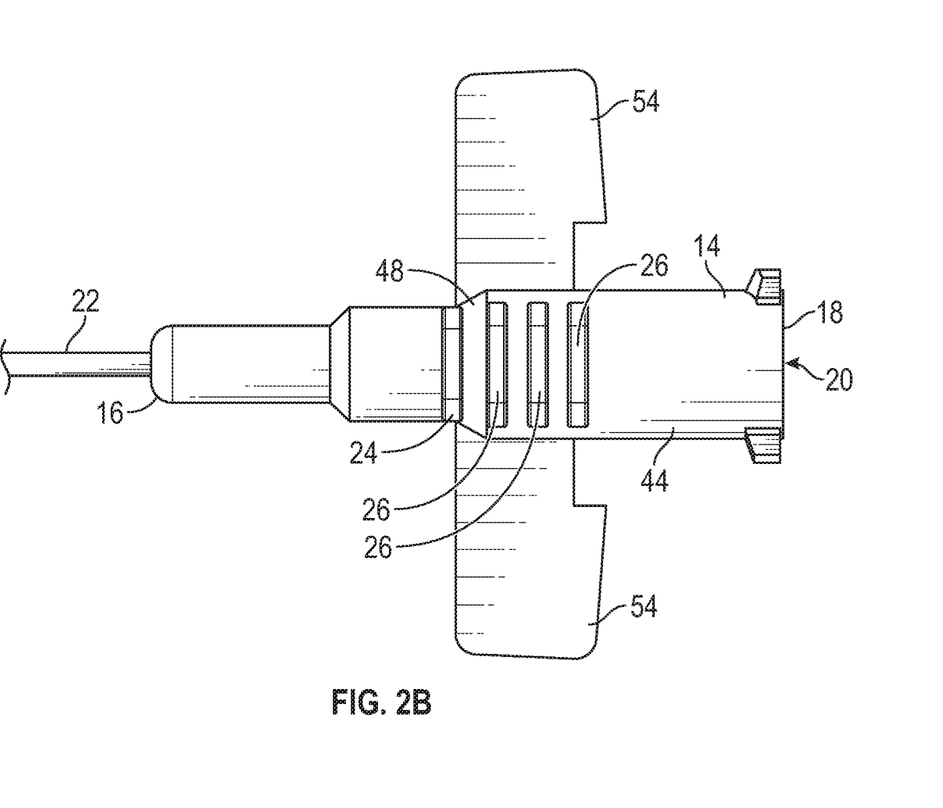
FIG. 2B is top view of the catheter hub of FIG. 2A, according to some embodiments.
Figure 2C:
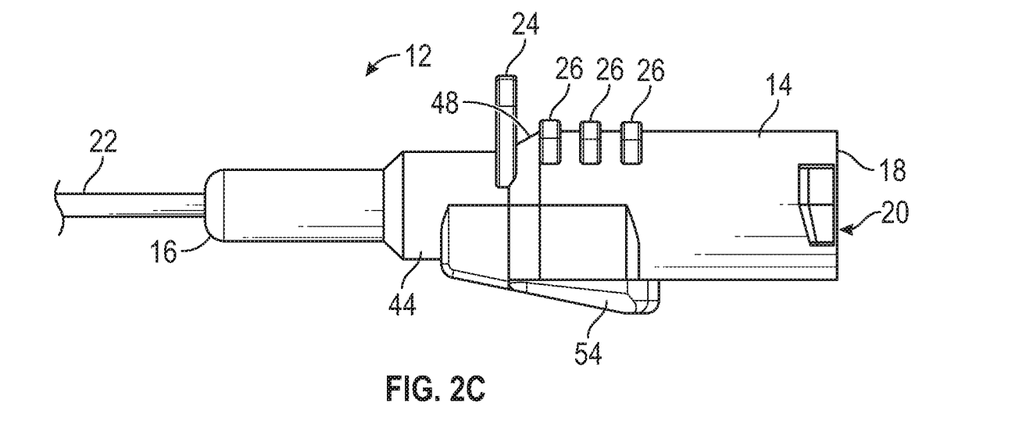
FIG. 2C is a side view of the catheter assembly of FIG. 2A, according to some embodiments.

In some embodiments, the ribs 26 may be anti-rotation features to reduce or prevent free spinning of the catheter hub 14 through contact with a first digit of a user during insertion, hooding, and threading. In some embodiments, the ribs 26 may oppose rotational movement of the catheter hub 14 and enhance the stability of the catheter tube 22 during insertion, hooding, and threading. In some embodiments, the push tab 24 and/or the ribs 26 may be described in U.S. patent application Ser. No. 16/570,713, filed Sep. 13, 2019, entitled "MEDICAL DEVICE WITH ANTI-ROTATION PUSH TAB," which is hereby incorporated by reference in its entirety.

In some embodiments, the ribs 26 may be generally parallel to each other. In some embodiments, the ribs 26 and/or the push tab 24 may be evenly spaced apart. In some embodiments, an upper surface of each of the ribs 26 may be concave, which may support the curvature of the first digit. In some embodiments, the ribs 26 and/or the push tab 24 may be generally perpendicular to the longitudinal axis 42 of the catheter system 10. In some embodiments, each of the ribs 26 may include a same width generally perpendicular to the longitudinal axis 42 of the catheter system 10. In some embodiments, one or more of the ribs 26 may be a same height. In some embodiments, features of the ribs 26 may facilitate contact between the first digit of the user and the push tab 24 and the ribs 26.

Figure 1A:
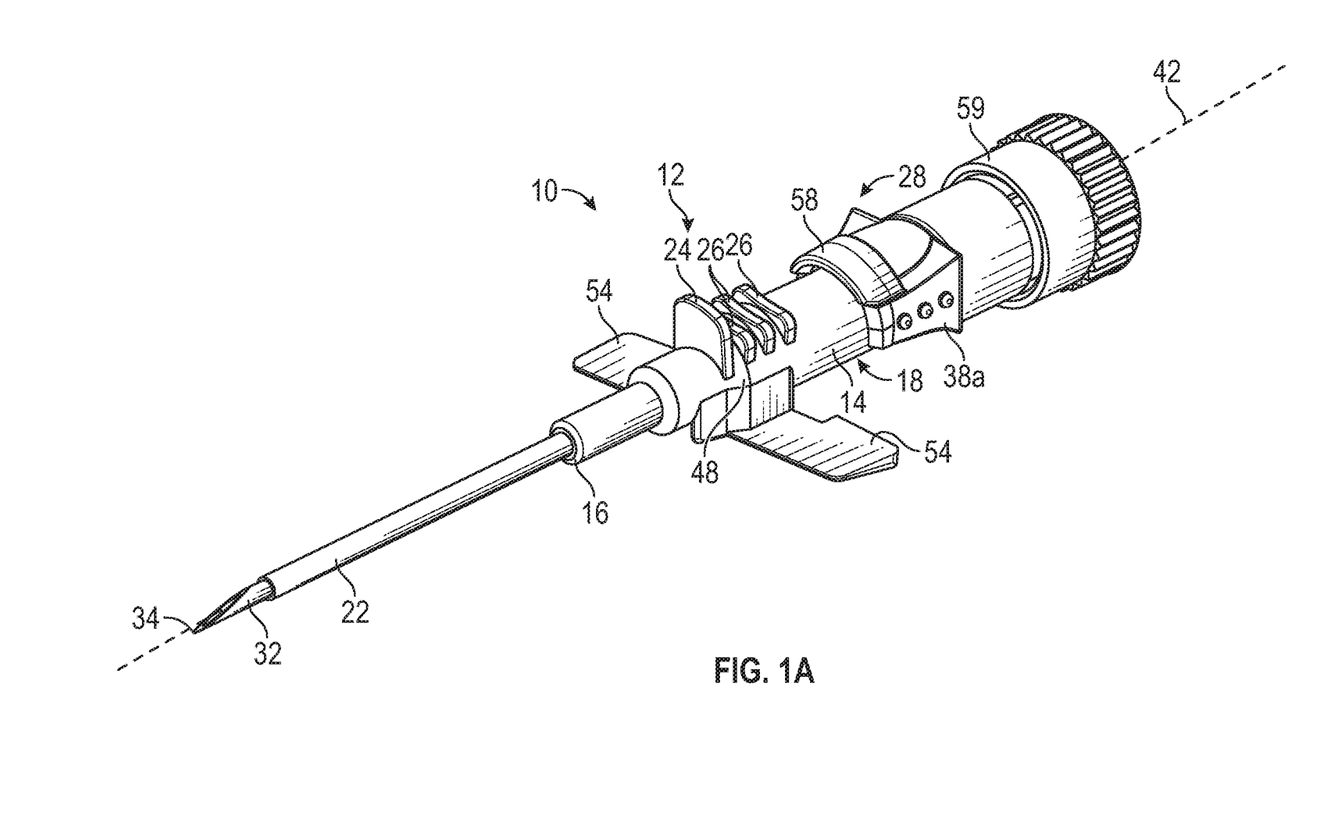
FIG. 1A is an upper perspective view of an example catheter system, according to some embodiments.

In some embodiments, the catheter system 10 may include a needle assembly 28, which may include a needle hub 30 and an introducer needle 32 extending distally from the needle hub 30 and through the catheter tube 22. In some embodiments, a proximal end of the introducer needle 32 may be secured within the needle hub 30. In some embodiments, the introducer needle 32 may include a sharp distal tip 34 to facilitate insertion of the catheter tube 22 into a vein of the patient. In some embodiments, a bevel of the sharp distal tip 34 of the introducer needle 32 may face upwardly when the catheter system 10 is in an insertion configuration, as illustrated in FIG. 1A.

In some embodiments, the introducer needle 32 may be constructed of stainless steel or another suitable material. In some embodiments, the catheter hub 14 and/or the needle hub 30 may be constructed of a relatively flexible plastic or another suitable material. In some embodiments, the catheter tube 22 may be constructed of thermoplastic polyurethane ("TPU") or another suitable material.

Figure 3A:
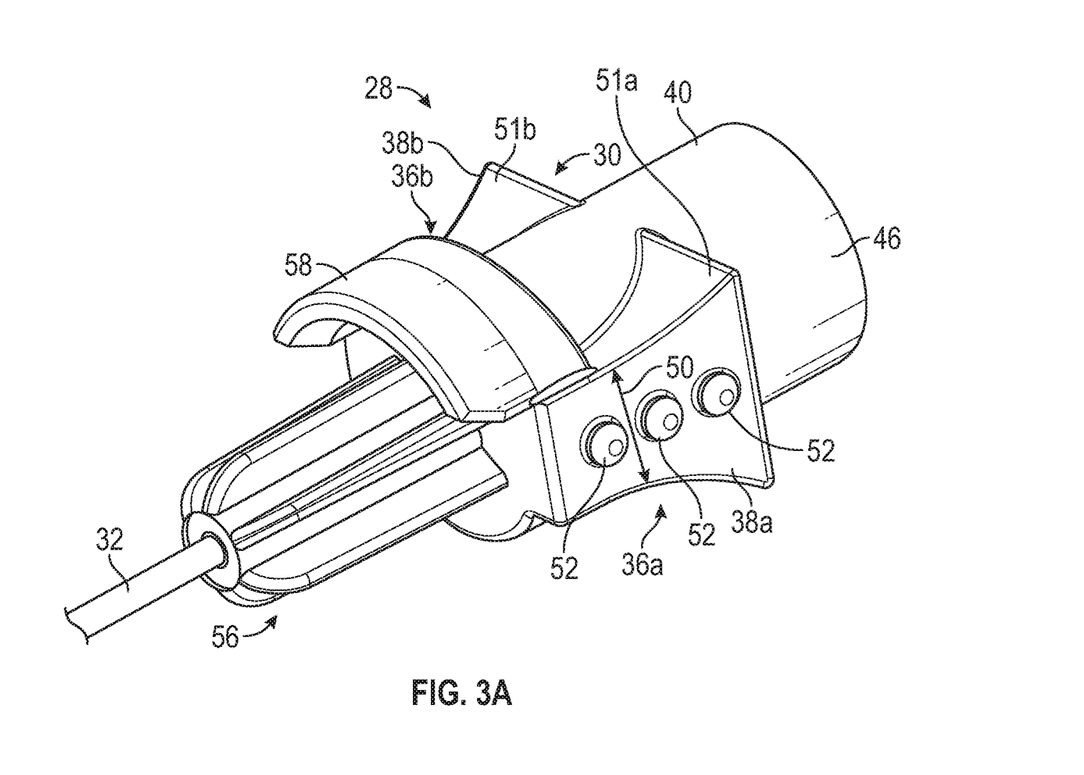
FIG. 3A is an upper perspective view of an example needle assembly of the catheter system of FIG. 1A, according to some embodiments.
Figure 3B:
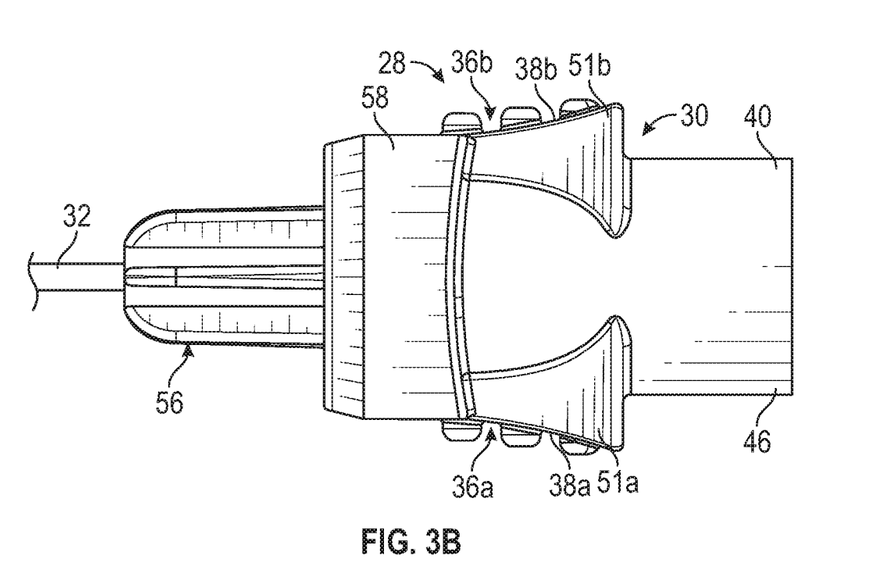
FIG. 3B is top view of the needle assembly of FIG. 3A, according to some embodiments.
Figure 3C:
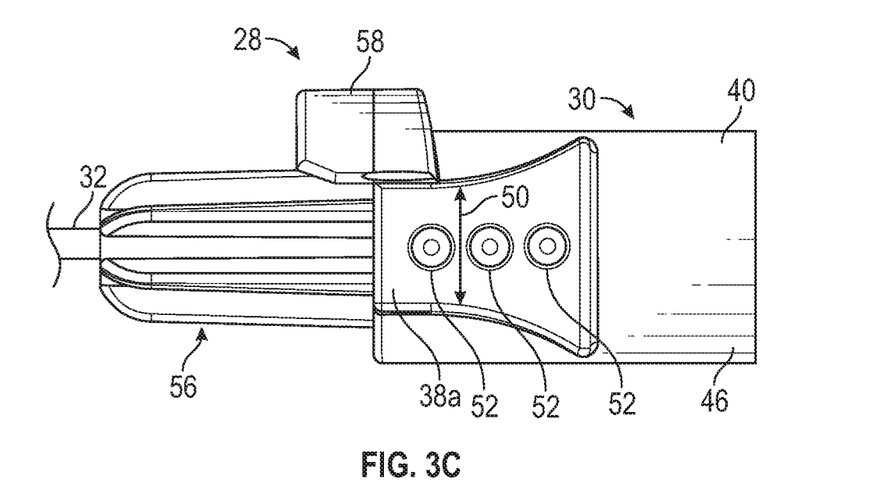
FIG. 3C is a side view of the needle assembly of FIG. 3A, according to some embodiments.

In some embodiments, the needle hub 30 may include a first grip 36a and/or a second grip 36b. In some embodiments, the first grip 36a may include a first face 38a and/or the second grip 36b may include a second face 38b opposite the first face 38a. In some embodiments, the first face 38a and/or the second face 38b may be positioned outwardly from the catheter hub 14 and a body 40 of the needle hub 30. In further detail, in some embodiments, the first face 38a and/or the second face 38b may be positioned further away from a longitudinal axis 42 of the catheter system 10 than an outer surface 44 of the catheter hub 14 and an outer surface 46 of the body 40 of the needle hub 30. In some embodiments, the body 40 of the needle hub 30 may be generally cylindrical.

In some embodiments, the catheter hub 14 may include a stepped or tapered outer surface 48 disposed between the distal end 16 of the catheter hub 14 and the proximal end 18 of the catheter hub 14. In some embodiments, the stepped or tapered outer surface 48 may be annular or semi-annular. In some embodiments, an outer diameter of the catheter hub 14 may be generally uniform immediately distal and immediately proximal to the stepped or tapered outer surface 48.

Figure 1B:
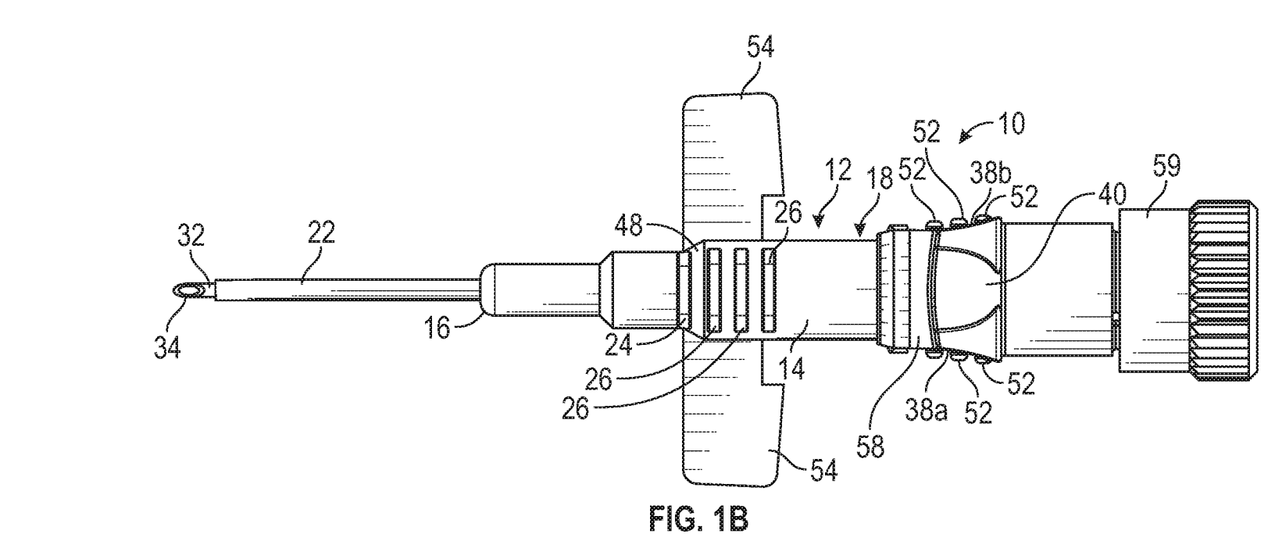
FIG. 1B is top view of the catheter system of FIG. 1A, according to some embodiments.
Figure 1C:
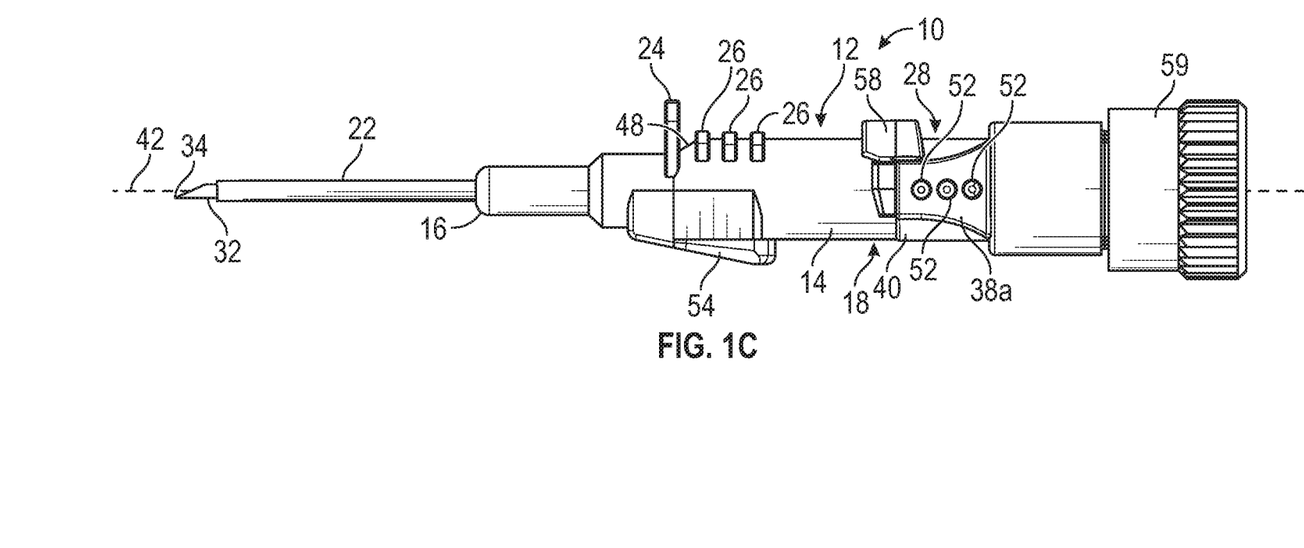
FIG. 1C is a side view of the catheter system of FIG. 1A, according to some embodiments.

In some embodiments, the push tab 24 may be distal and/or proximate to the stepped or tapered outer surface 48. In some embodiments, the push tab 24 distal and/or proximate the stepped or tapered outer surface 48 may facilitate simultaneous placement of the first digit of a user on the push tab 24 and second and third digits on the first face 38a and the second face 38b, respectively. In some embodiments, the push tab 24 distal and/or proximate the stepped or tapered outer surface 48 may facilitate accommodation of a length, position, and curvature of the first digit when the second digit and the third digit are placed on the first face 38a and the second face 38b, respectively. In some embodiments, the first digit of the user may push in a distal direction on the push tab 24 to advance the catheter hub 14 distally with respect to the needle hub 30, and the second digit and the third digit may remain generally stationary. In some embodiments, the first digit may be disposed between the second digit and the third digit on a hand of the user. The first digit may correspond to, for example, a pointer finger of the user.

In some embodiments, a diameter 50 of the first face 38a and/or the second face 38b may increase in a proximal direction. In some embodiments, the first face 38a and/or the second face 38b may be concave. Thus, in some embodiments, the first face 38a and/or the second face 38b may conform to a curvature of digits of the user. In some embodiments, the first grip 36a may include a top surface 51a, which may extend outwardly from the body 40 of the needle hub 30 to the first face 38a. In some embodiments, the second grip 36b may include a top surface 51b, which may extend outwardly from the body 40 of the needle hub 30 to the second face 38b. In some embodiments, a distal-most rib of the plurality of ribs 26 may be proximal and/or proximate the stepped or tapered outer surface 48. In these and other embodiments, the push tab 24 and the ribs 26 may conform to a curvature of the first digit, facilitating contact of the push tab 24 and the ribs 26 with the first digit.

In some embodiments, the first face 38a and/or the second face 38b may include one or more protrusions 52, which may enhance a tactile feel for the user with regard to placement of the digits of the user and assist in maintaining the digits of the user on the first face 38a and/or the second face 38b. In some embodiments, the protrusions 52 may be arranged linearly and/or along a length of the first face 38a and/or the second face 38b, which may facilitate contact along a length of a particular digit of the user.

In some embodiments, the catheter system 10 may include one or more wings 54, which may extend outwardly from the catheter hub 14. In some embodiments, the push tab 24 and at least one of the ribs 26 may be aligned with the wings 54, which may decrease a likelihood interference of the second digit and/or the third digit with any securement tape or dressing coupled to the wings 54. In some embodiments, the wings 54 may extend from a lower portion of the catheter hub 14. In some embodiments, the wings 54 may be configured to fold to an upward and/or downward position. In some embodiments, the catheter hub 14 may be straight with no side ports between the distal end 16 and the proximal end 18. In some embodiments, the catheter hub 14 may include one or more side ports. In some embodiments, the catheter system 10 may include one or more features of the Becton Dickinson NEOFLON IV Cannula System but a wing housing with a corresponding push tab on the wing housing may be removed. In these and other embodiments, the catheter system 10 may have a reduced or compact size.

In some embodiments, the needle hub 30 may be removably coupled to the catheter hub 14 via a male luer of the needle hub 30 or another suitable connector. In some embodiments, the needle hub 30 may include an extension 56, which may extend into the proximal end 18 of the catheter hub 14. In some embodiments, a distal end of the needle hub 30 may include a flange 58, which may extend at least partially around a circumference of the body 40 of the needle hub 30. In some embodiments, the flange 58 may extend distally beyond the proximal end 18 of the catheter hub 14. In some embodiments, the flange 58 may extend from the first grip 36a to the second grip 36b. In some embodiments, the flange 58 may extend from the first face 38a to the second face 38b. In some embodiments, a vent plug 59 may be inserted in a proximal end of the needle hub 30, which may provide venting for blood flashback within the catheter system 10.

In some embodiments, the catheter system 10 may include a safety feature, which may shield the sharp distal tip 34 of the introducer needle 32 when the introducer needle 32 is withdrawn from the catheter hub 14. In some embodiments, the safety feature may be passive, such that no activation is required by the user. In some embodiments, the safety feature may include an active safety feature that is activated by the user.

It is understood that the catheter system 10 may include any suitable active or passive safety mechanisms. In some embodiments, the safety feature may include an internal interlock in which the safety feature is coupled with an internal surface of the catheter hub 14. Non-limiting examples of safety features that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety.

In some embodiments, the safety feature may include an external interlock in which the safety feature is coupled with an external surface of the catheter hub 14. Non-limiting examples of safety features that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety.

In some embodiments, the safety feature may include a clip disposed within the catheter hub 14, a non-limiting example of which is provided in U.S. Pat. No. 6,117,108, titled SPRING CLIP SAFETY IV CATHETER, filed Jun. 12, 1998, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the V-clip may selectively retain a portion of the catheter hub 14.

Referring now to FIGS. 4A-6C, a catheter system 60 is illustrated, according to some embodiments. In some embodiments, the catheter system 60 may be similar or identical in terms of one or more included components and/or operation to the catheter system 10 discussed with respect to FIGS. 1A-3B. In some embodiments, the needle hub 30 may include a first elliptical face 62a and/or the second elliptical face 62b. In some embodiments, the first elliptical face 62a and the second elliptical face 62b may be similar or identical in terms of one or more included components and/or operation to the first face 38a and the second face 38b, respectively, discussed with respect to FIGS. 1A-3B.

Figure 6A:
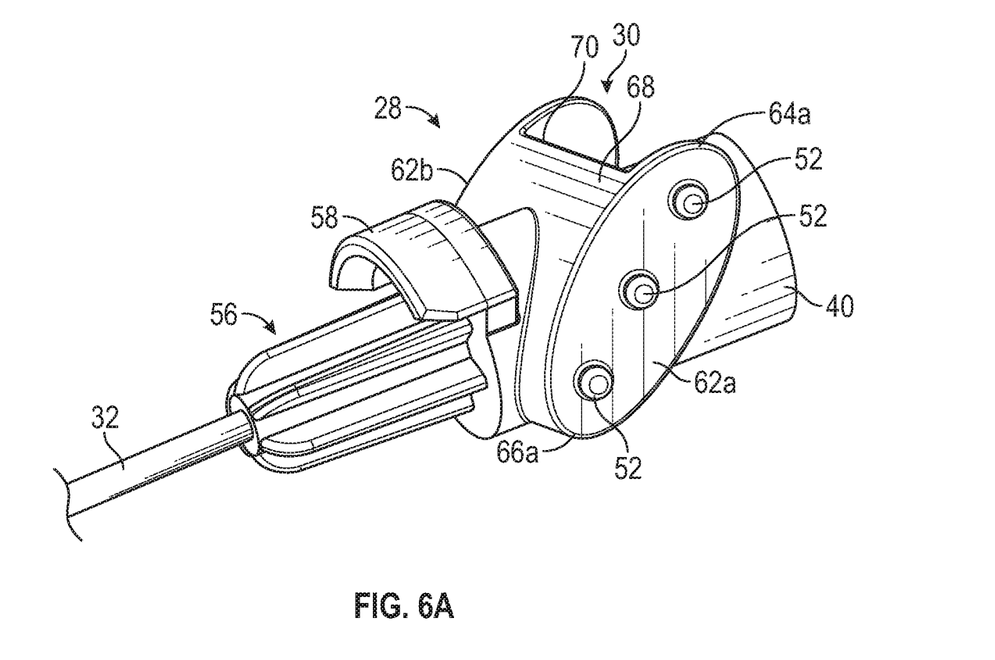
FIG. 6A is an upper perspective view of an example needle assembly of the catheter system of FIG. 4A, according to some embodiments.
Figure 6B:
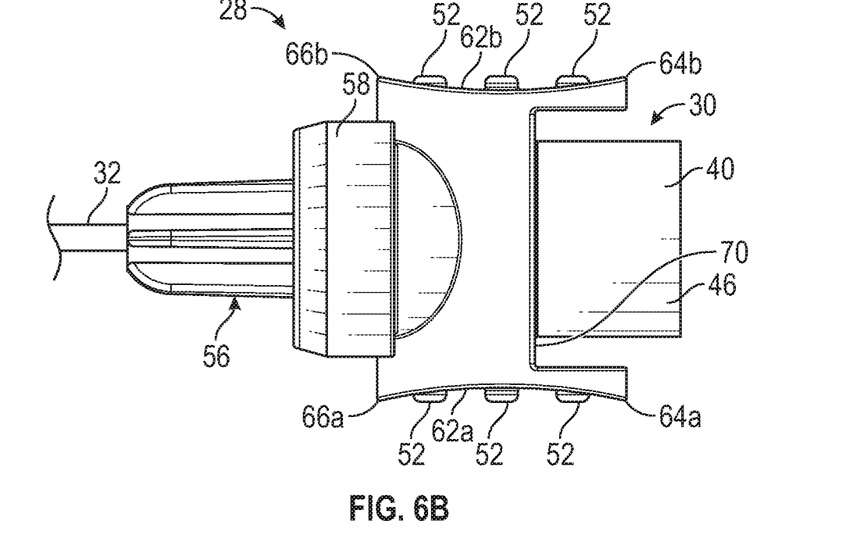
FIG. 6B is top view of the needle assembly of FIG. 6A, according to some embodiments.
Figure 6C:
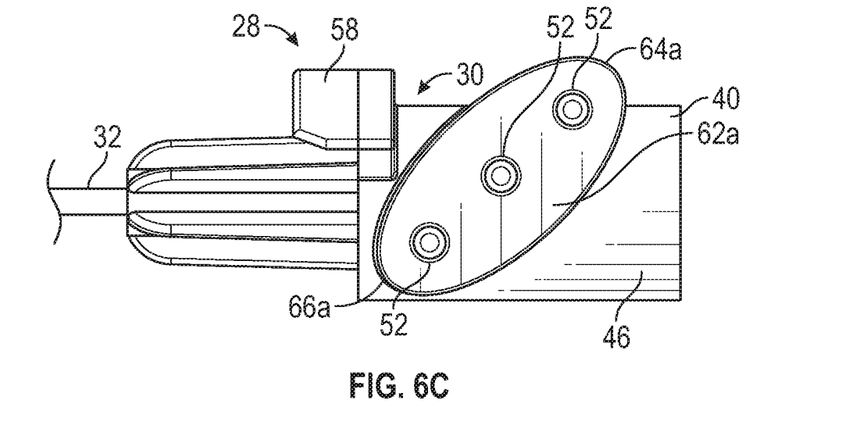
FIG. 6C is a side view of the needle assembly of FIG. 6A, according to some embodiments.

In some embodiments, the first elliptical face 62a and/or the second elliptical face 62b may be positioned outwardly from the catheter hub 14 and the body 40 of the needle hub 30. In some embodiments, the first elliptical face 62a may be angled with respect to the longitudinal axis 42 of the catheter system 60 such that a proximal end 64a of the first elliptical face 62a is positioned upwardly with respect to a distal end 66a of the first elliptical face 62a. In some embodiments, the second elliptical face 62b may be angled with respect to the longitudinal axis 42 of the catheter system 60 such that a proximal end 64b of the second elliptical face 62b is positioned upwardly with respect to a distal end 66b of the second elliptical face 62b.

Figure 4A:
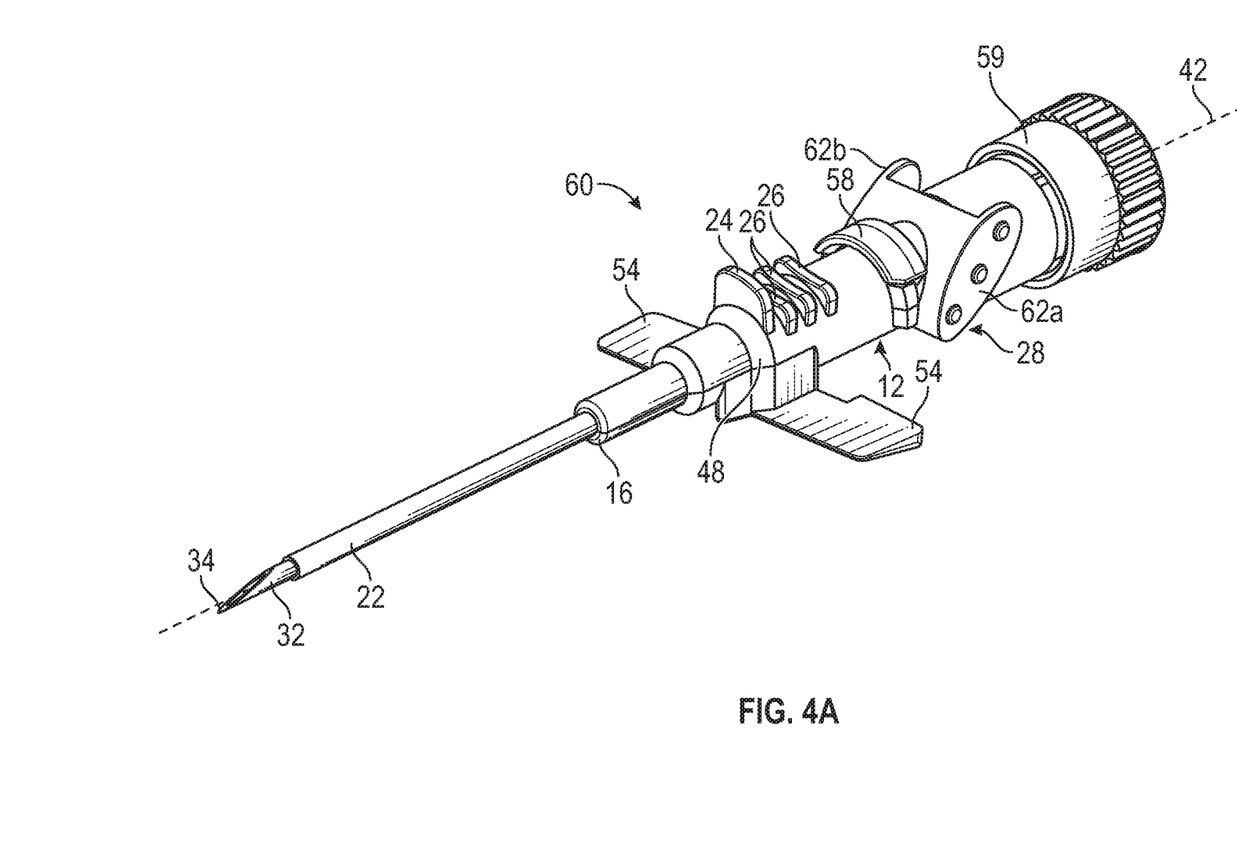
FIG. 4A is an upper perspective view of another example catheter system, according to some embodiments.
Figure 4B:
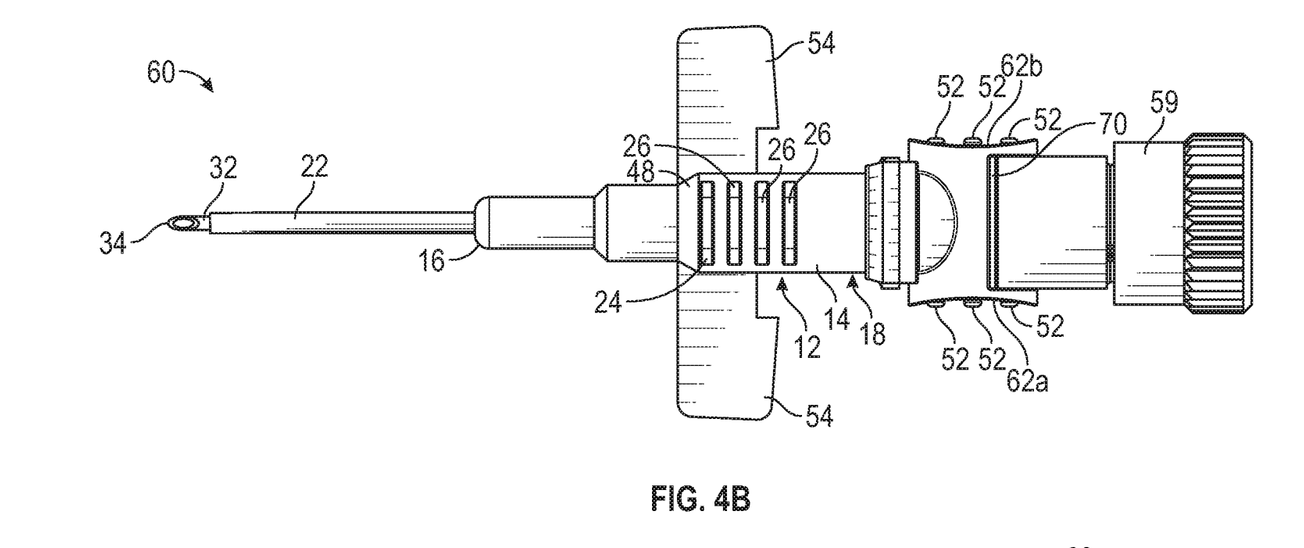
FIG. 4B is top view of the catheter system of FIG. 4A, according to some embodiments.
Figure 4C:
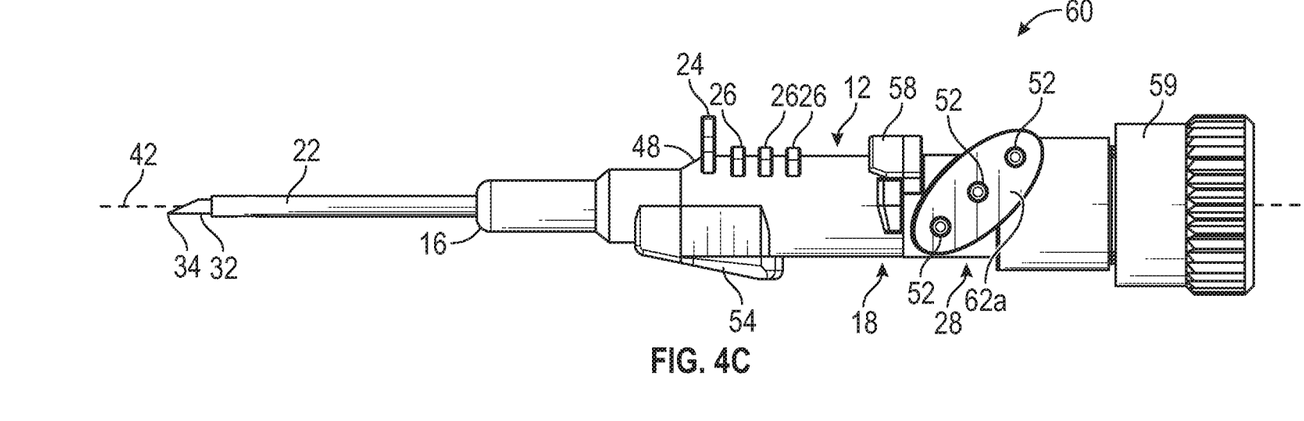
FIG. 4C is a side view of the catheter system of FIG. 4A, according to some embodiments.
Figure 5A:
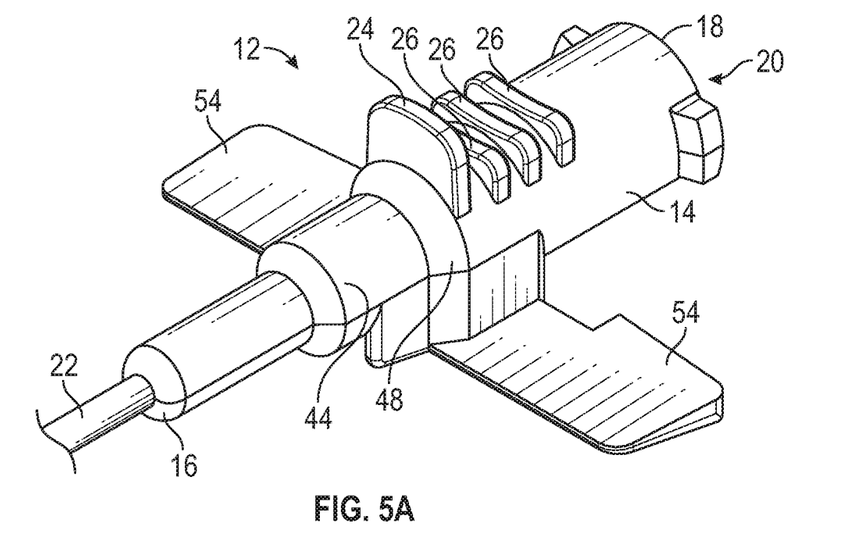
FIG. 5A is an upper perspective view of an example catheter hub of the catheter system of FIG. 4A, according to some embodiments.
Figure 5B:
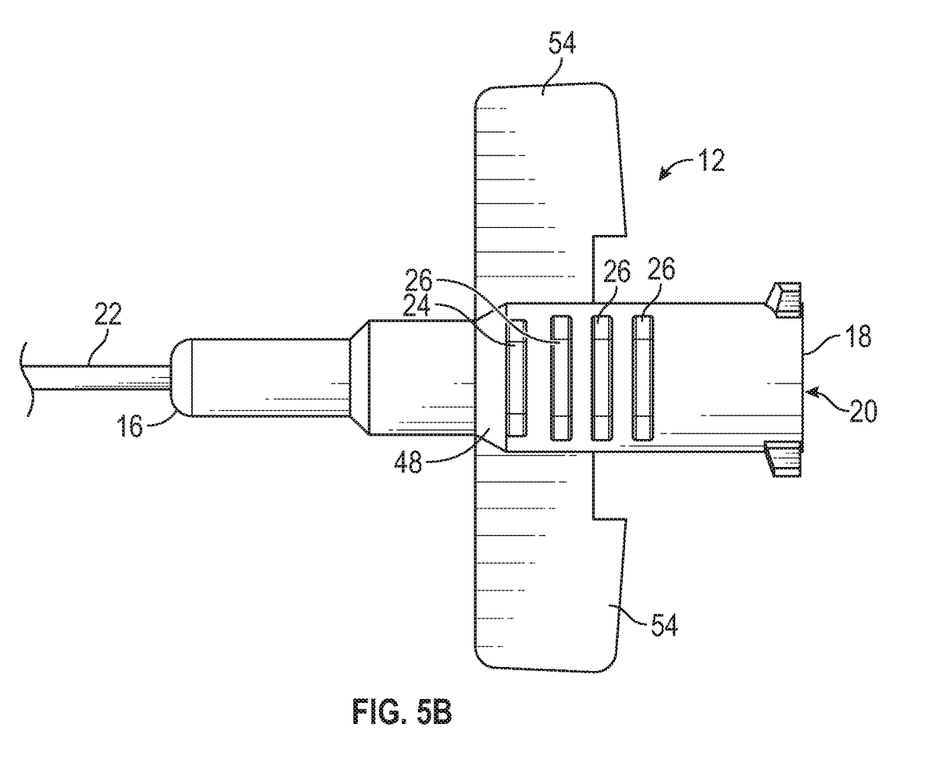
FIG. 5B is top view of the catheter hub of FIG. 5A, according to some embodiments.
Figure 5C:
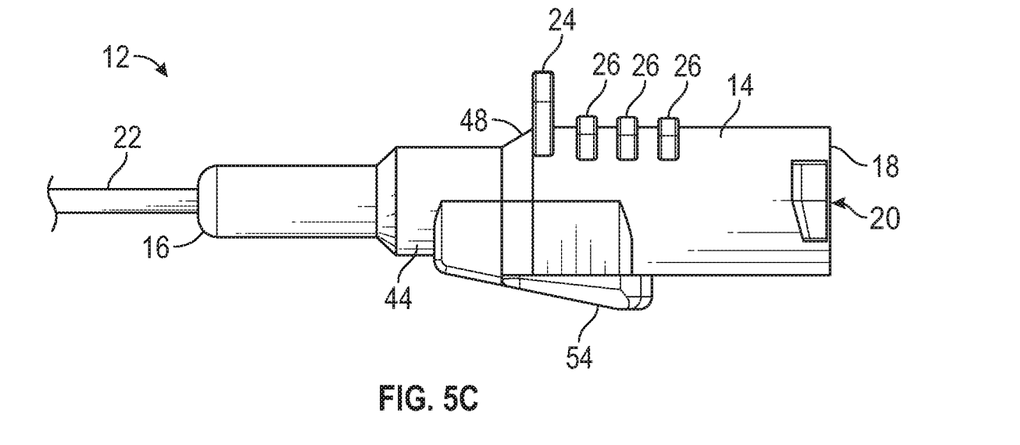
FIG. 5C is a side view of the catheter assembly of FIG. 5A, according to some embodiments.

In some embodiments, the push tab 24 may be proximal and/or proximate the stepped or tapered outer surface 48. In some embodiments, the push tab 24 distal and/or proximate the stepped or tapered outer surface 48 may facilitate simultaneous placement of the first digit of the user on the push tab 24 and the second digit and third digit on the first elliptical face 62a and the second elliptical face 62b, respectively. In some embodiments, the push tab 24 distal and/or proximate the stepped or tapered outer surface 48 may facilitate accommodation of the length, position, and curvature of the first digit when the second digit and the third digit are placed on the first elliptical face 62a and the second elliptical face 62b, respectively. In some embodiments, the first digit of the user may push in a distal direction on the push tab to advance the catheter hub 14 distally with respect to the needle hub 30, while the second digit and the third digit may remain generally stationary.

In some embodiments, the first elliptical face 62a and/or the second elliptical face 62b may include the protrusions 52, which may enhance a tactile feel for the user with regard to placement of the digits of the user and assist in maintaining the digits of the user on the first elliptical face 62a and/or the second elliptical face 62b. In some embodiments, the protrusions 52 may be arranged linearly and/or along a length of the first elliptical face 62a and/or the second elliptical face 62b, which may facilitate contact along a length of a particular digit of the user.

In some embodiments, the first elliptical face 62a and the second elliptical face 62b may be spaced apart by a grip body 68. In some embodiments, the first elliptical face 62a and/or the second elliptical face 62b may extend proximally beyond the grip body 68 to form a notch 70, which may decrease a likelihood of the hand of the user contacting and/or applying pressure of a top of the needle hub 30.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
 a catheter assembly, comprising:
  a catheter hub, comprising a distal end, a proximal end, a lumen extending through the distal end and the proximal end, and a stepped or tapered outer surface disposed between the distal end and the proximal end;
  a catheter tube extending distally from the distal end of the catheter hub;
  a push tab and a plurality of ribs extending outwardly from an upper portion of the catheter hub, wherein the plurality of ribs are shorter in height than the push tab and proximal to the push tab, wherein the push tab is distal to the stepped or tapered outer surface; and
  a first wing and a second wing extending outwardly from the catheter hub, wherein multiple of the plurality of ribs are disposed between the first wing and the second wing; and
 a needle assembly, wherein the needle assembly comprises a needle hub and an introducer needle extending distally from the needle hub and through the catheter tube, wherein the needle hub comprises a first grip and a second grip, wherein the first grip comprises a first face and the second grip comprises a second face opposite the first face, wherein the first face and the second face are positioned outwardly from a body of the needle hub, wherein the first face and the second face are elliptical, wherein the first face is angled with respect to a longitudinal axis of the catheter system such that a proximal end of the first face is positioned upwardly with respect to a distal end of the first face, wherein the second face is angled with respect to the longitudinal axis of the catheter system such that a proximal end of the second face is positioned upwardly with respect to a distal end of the second face.

2. The catheter system of claim 1, wherein a diameter of the first face and a diameter of the second face increase in a proximal direction.

3. The catheter system of claim 1, wherein the first face and the second face are concave.

4. The catheter system of claim 1, wherein the first face and the second face comprise a plurality of protrusions.

5. The catheter system of claim 1, wherein a distal-most rib of the plurality of ribs is proximal to the stepped or tapered outer surface.

6. The catheter system of claim 1, wherein the push tab and at least one of the plurality of ribs are aligned with the first wing and the second wing.

7. A catheter system, comprising:
 a catheter assembly, comprising:
  a catheter hub, comprising a distal end, a proximal end, a lumen extending through the distal end and the proximal end, and a stepped or tapered outer surface disposed between the distal end and the proximal end;
  a catheter tube extending distally from the distal end of the catheter hub; and
  a push tab and a plurality of ribs extending outwardly from an upper portion of the catheter hub, wherein the plurality of ribs are shorter in height than the push tab and proximal to the push tab, wherein the push tab is proximal to the stepped or tapered outer surface; and
 a needle assembly, wherein the needle assembly comprises a needle hub and an introducer needle extending distally from the needle hub and through the catheter tube, wherein the needle hub comprises a first elliptical face and a second elliptical face opposite the first elliptical face, wherein the first elliptical face and the second elliptical face are positioned outwardly from a body of the needle hub, wherein a longitudinal axis of the first elliptical face is angled with respect to a longitudinal axis of the catheter system such that a proximal end of the first elliptical face is positioned upwardly with respect to a distal end of the first elliptical face, wherein a longitudinal axis of the second elliptical face is angled with respect to the longitudinal axis of the catheter system such that a proximal end of the second elliptical face is positioned upwardly with respect to a distal end of the second elliptical face, wherein the first elliptical face comprises a plurality of protrusions arranged along the longitudinal axis of the first elliptical face and angled with respect to the longitudinal axis of the catheter system, wherein the second elliptical face comprises another plurality of protrusions arranged along the longitudinal axis of the second elliptical face and angled with respect to the longitudinal axis of the catheter system.

8. The catheter system of claim 7, wherein the push tab is proximate the stepped or tapered outer surface.

9. The catheter system of claim 7, wherein the first elliptical face and the second elliptical face are spaced apart by a grip body, wherein the first elliptical face and the second elliptical face extend proximally beyond the grip body to form a notch.

10. A catheter system, comprising:
 a catheter assembly, comprising:
  a catheter hub, comprising a distal end, a proximal end, a lumen disposed between the distal end and the proximal end,
  a catheter tube extending distally from the distal end of the catheter hub; and
  a push tab and a plurality of ribs extending outwardly from an upper portion of the catheter hub, wherein the plurality of ribs are shorter in height than the push tab and proximal to the push tab;
  a first wing and a second wing extending outwardly from the catheter hub, wherein multiple of the plurality of ribs are disposed between the first wing and the second wing; and
 a needle assembly, comprising a needle hub, an introducer needle extending distally from the needle hub and through the catheter tube, and a grip coupled to the needle hub, wherein the grip comprises a face disposed outwardly from the push tab and the plurality of ribs, wherein the face is a first face, wherein the grip further comprises a second face opposite the first face, wherein the first face and the second face are elliptical, wherein the first face is angled with respect to a longitudinal axis of the catheter system such that a proximal end of the first face is positioned upwardly with respect to a distal end of the first face, wherein the second face is angled with respect to the longitudinal axis of the catheter system such that a proximal end of the second face is positioned upwardly with respect to a distal end of the second face.

11. The catheter system of claim 10, wherein the catheter hub comprises a stepped or tapered outer surface, wherein the push tab is distal to and proximate the stepped or tapered outer surface.

12. The catheter system of claim 11, wherein a distal-most rib of the plurality of ribs is proximal to the stepped or tapered outer surface.

13. The catheter system of claim 10, wherein the catheter hub comprises a stepped or tapered outer surface, wherein the push tab is proximal to the stepped or tapered outer surface.

14. The catheter system of claim 10, wherein the first face and the second face are positioned outwardly from a body of the needle hub, wherein a diameter of the first face and a diameter of the second face increase in a proximal direction.

15. The catheter system of claim 14, wherein a longitudinal axis of the first face and a longitudinal axis of the second face are generally aligned with the longitudinal axis of the catheter system.

16. The catheter system of claim 10, wherein the push tab and at least one of the plurality of ribs are aligned with the first wing and the second wing.

\* \* \* \* \*